(12) United States Patent
Dabney

(10) Patent No.: US 9,504,848 B2
(45) Date of Patent: Nov. 29, 2016

(54) MEDICAL DEVICES WITH A LIGHT SOURCE AND ANTIMICROBIAL SOLUTION

(71) Applicant: Paul Dabney, Georgetown, TX (US)

(72) Inventor: Paul Dabney, Georgetown, TX (US)

(73) Assignee: DABNEY PATENTS, L.L.C., Georgetown, TX (US)

( * ) Notice: Subject to any disclaimer, the term of this patent is extended or adjusted under 35 U.S.C. 154(b) by 170 days.

(21) Appl. No.: 14/536,633

(22) Filed: Nov. 9, 2014

(65) Prior Publication Data
US 2016/0015998 A1    Jan. 21, 2016

Related U.S. Application Data

(63) Continuation-in-part of application No. 14/497,269, filed on Sep. 25, 2014.

(60) Provisional application No. 62/026,498, filed on Jul. 18, 2014.

(51) Int. Cl.
| | |
|---|---|
| *A61N 5/06* | (2006.01) |
| *A01N 59/00* | (2006.01) |
| *A61C 19/06* | (2006.01) |

(52) U.S. Cl.
CPC ............... *A61N 5/062* (2013.01); *A01N 59/00* (2013.01); *A61C 19/063* (2013.01); *A61N 5/0601* (2013.01); *A61N 5/0624* (2013.01); *A61N 2005/063* (2013.01); *A61N 2005/0636* (2013.01); *A61N 2005/0645* (2013.01); *A61N 2005/0647* (2013.01)

(58) Field of Classification Search
CPC .... A61C 19/06; A61C 19/063; A61C 1/088; A61M 5/445; A61M 25/0043; A61N 5/0616; A61N 2005/0662; A61K 33/40; A61K 31/65; A61K 31/7056; A61K 47/22; A61K 31/7048; A61K 31/203; A61K 31/60
See application file for complete search history.

(56) References Cited

U.S. PATENT DOCUMENTS

| | | | | |
|---|---|---|---|---|
| 8,439,674 B2* | 5/2013 | Li | ................. | A61C 19/063 433/24 |
| 8,591,229 B2* | 11/2013 | Keller | ................. | A61C 19/063 433/80 |
| 2009/0018424 A1* | 1/2009 | Kamath | ............. | A61B 5/14542 600/347 |

* cited by examiner

*Primary Examiner* — Rex R Holmes
(74) *Attorney, Agent, or Firm* — Maier & Maier, PLLC

(57) ABSTRACT

Medical devices with a light source and antimicrobial solution include a solution retainer adapted to retain an antimicrobial solution against a user; a fiber optic cable; a light termination on the fiber optic cable that provides light from the fiber optic cable to the antimicrobial solution in the solution retainer; and a light source that provides a light of a predetermined wavelength to the fiber optic cable. Medical device includes a container, a bowl, a full body suit, garments for body parts, a helmet, and a catheter.

17 Claims, 4 Drawing Sheets

MEDICAL DEVICES WITH A LIGHT SOURCE AND ANTIMICROBIAL SOLUTION

RELATED APPLICATIONS

This application claims the benefit of the filing date of U.S. Patent Application No. 62/026,498, filed Jul. 18, 2014, which is incorporated herein by reference in its entirety, and U.S. patent application Ser. No. 14/497,269, filed Sep. 24, 2014, which is incorporated herein by reference in its entirety.

BACKGROUND OF THE INVENTION

The present invention generally relates to enhancement of antimicrobial solutions and more specifically to medical devices with a light source and antimicrobial solutions.

Microbes exist that cause harm or disease in living tissues.

Light of certain wavelengths has been demonstrated to improve or "super-charge" the effects of certain antimicrobial or anti-microbial agents, creating a synergistic effect to destroy or inhibit microbial growth.

Most chemical reactions work best at a certain temperature. These ideal temperatures vary for each reaction. A "scalding chart" might indicate that water of 130 degrees is safe under an exposure of 30 seconds, but over that it causes burns. Water of 120 degrees may be safe up to 5 minutes.

It would be desirable to add light of certain wavelengths to a device that holds certain antimicrobial agents in close proximity to tissues, so a synergistic effect can be created to destroy or inhibit microbial growth on the tissues.

SUMMARY OF THE INVENTION

In one aspect of the present invention, a device includes a solution retainer adapted to retain an antimicrobial solution against a user; a fiber optic cable; a light termination on the fiber optic cable that provides light from the fiber optic cable to the antimicrobial solution in the solution retainer; and a light source that provides a light of a predetermined wavelength to the fiber optic cable.

In additional aspects of the present invention, a medical device includes a container, a bowl, a full body suit, garments for body parts, a helmet, and a catheter.

DETAILED DESCRIPTION

Figure 2:
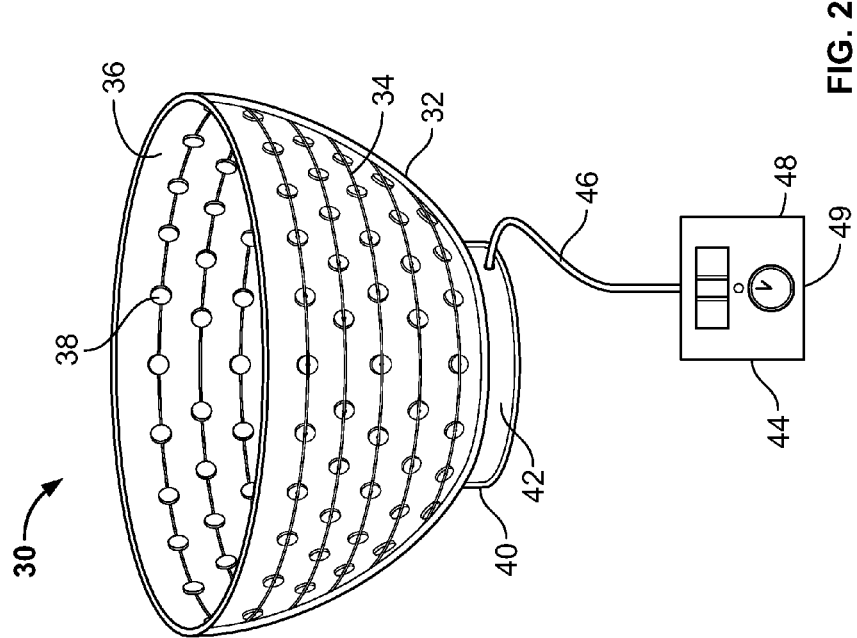
FIG. 2 depicts an embodiment of a bowl according to the present invention.

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order.

An embodiment of the present invention generally provides a device to hold solutions in contact with tissues, such as flesh or teeth, while the tissues and solutions are simultaneously being exposed to certain wavelengths of light. This device has a component that amplifies the effect of the antimicrobial solutions by using a certain wavelength of light. The antimicrobial solution may or may not be light activated at any given time. When the light is on, the solution is "supercharged" by the light. This synergistic effect eliminates or reduces more microbes than the solution acting alone.

Microbes exist that cause harm or disease in living tissues. By adding a light of certain wavelengths to a device that holds certain antimicrobial agents in close proximity to tissues, a synergistic effect can be created to destroy or inhibit microbial growth. In the oral cavity, this device could be a tray designed to cover the teeth and gingival. This tray would emit certain wavelengths of light that when combined with certain antimicrobial solutions in the tray would cause a synergistic antimicrobial effect. The light could be produced, for example, from a light emitting diode (LED) or laser. An external light source could be connected to the fiber optic cable in the solution holding apparatus with a fiber optic connection cable that may also include a fiber optic connection interface or plug.

Embodiments of the present invention may create another means to treat disease. Super charging antimicrobial solutions with certain wavelengths of lights may cause the solutions to eliminate or reduce microbes at a higher percentage than the solution alone.

Embodiments may create a synergistic effect between certain wavelengths of light and antimicrobial solutions that when applied to tissues eliminates or reduces disease causing microorganisms.

Embodiments of the present invention may consist of a solution holding apparatus or medium that emits certain wavelengths of light into the solution. When this light and solution combination is applied to tissues, a synergistic effect is created that reduces or eliminates microorganisms that cause disease. The essential components are 1. The solution holding apparatus 2. A light source 3. An antimicrobial solution.

Embodiments may utilize blue light, or another certain predetermined wavelength of light that supercharges the solution, with an exposure from a few second to minutes. Embodiments may also use an H2O2 solution, such as a gel, with concentration of 0.3 mM or any concentration of solution that is suitable as an antimicrobial agent.

In an embodiment, for safety, a "scalding chart" might indicate that water of 130 degrees is safe under an exposure of 30 seconds, but over that it causes burns. Water of 120 degrees may be safe up to 5 minutes. Hydrogen peroxide (H2O2), when it is exposed to a light of 400-500 nanometers wavelength, may kill 96% of microbes in less than 20 seconds. This solution may work best at 57 degrees Celsius (134 degrees F.).

Alternate embodiments may include heating elements that warm and further super-charge the antimicrobial solution. In embodiments, a device may contain heating or cooling components or both. In an embodiment, an antimicrobial solution may be preheated to an ideal or optimal temperature before it is exposed to synergizing light. For example, Hydrogen peroxide may preferably be exposed to a light of 400-500 nanometers at 57 degrees Celsius (134 degrees F.) for less than 20 seconds. Other chemicals may have different preferred temperatures.

Embodiments of a medical device may include integrated or internal heating elements that run adjacent to the light emitting cable in the device. Embodiments of integrated heating elements may be located in only a portion of the device, such as at the bottom of a container or garment. Heating elements may draw power from the same source as the light source, such as batteries or wall power. Power may be supplied to the heating elements in the device through the fiber optic connection cable or through a power connection cable that runs alongside the connection cable.

Alternate embodiments of heating elements may be separate from the portion of the device that retains the antimicrobial solution. Separate heating elements may warm the antimicrobial solution to an optimal temperature before the solution is added to the medical device, such as with a heating tray or oven, or may be used to apply heat to the antimicrobial solution in place, such as with a hot iron or wire.

Embodiments of a medical or dental device may include a light emitting fiber optic cable that may expose the antimicrobial solution to a certain wavelength of light, such as a purposefully selected wavelength or frequency of light from an LED or laser. A tray or other retainer for holding liquids may hold the antimicrobial solution. An embodiment may include a plurality of light terminations or other light emitters on the light emitting fiber optic cable. Each light termination taps into the fiber optic cable to pipe some of the light out the top of the termination, thereby emitting light into the antimicrobial solution. The device may be adjustable, so that the terminations can be added or moved, or the quantity and locations of the light terminations may be measured to fit an individual user. The light terminations may be located within the tray or other retainer so that each light termination is will be positioned in a preselected location within the retainer, such as near portions of tissue to be treated. The fiber optic cable may be opaque with light emitters spaced along its length, or may be at least partially translucent to emit light along its length.

In an embodiment, a the fiber optic cable may connect to a light source through a fiber optic connection cable. The connection cable may enter the tray or retainer and optically connect with the fiber optic cable through a fiber optic connection interface so that the light source can be attached and removed after use. An embodiment of the interface may include a fiber optic connection cable fixed to the fiber optic cable. Another embodiment of the interface may include a socket that mates with a plug on the connection cable so that the light source can be attached and removed after use.

Container.

An embodiment of a medical device may include a container to immerse a user's foot, hoof, head, leg, or other tissue in an antimicrobial solution while exposing it to a certain, predetermined wavelength of light. An embodiment may include a container, such as a bucket or pail. Embodiments may be made of watertight material such as, for example, metal, plastic, or wood. Embodiments may include a cylinder or section of a cone having vertical or nearly vertical walls, a flat bottom and an open top. Embodiments may include a hooped or arched carrying handle. A fiber optic cable may wrap up the inside surface of an inner wall of the container. The fiber optic cable may have light terminations spaced along the fiber optic cable inside the container. An embodiment may include a heating element inside the container. The heating element may include a coil or coils at the bottom of the container, which may be located in a circle or partial circle around the inner wall at the bottom of a bucket. The heating element may include heating wires inside the container that run adjacent to the fiber optic cable. The fiber optic cable may connect through a connection cable to a light source. A connection interface or plug may connect and release an external light source from the container. The heating element may receive power from the light source, through the same light source connection cable or through a separate power connection cable. A switch may allow the light source, the heating power, or both to be connected yet switched on or off.

To use an embodiment, a user may add anti-microbial solution to the container, turn on the heating element to warm the solution, immerse the body part into the container containing the warm solution, and turn on the light source. This will substantially illuminate any item immersed in the container from all sides of the item.

Figure 1:
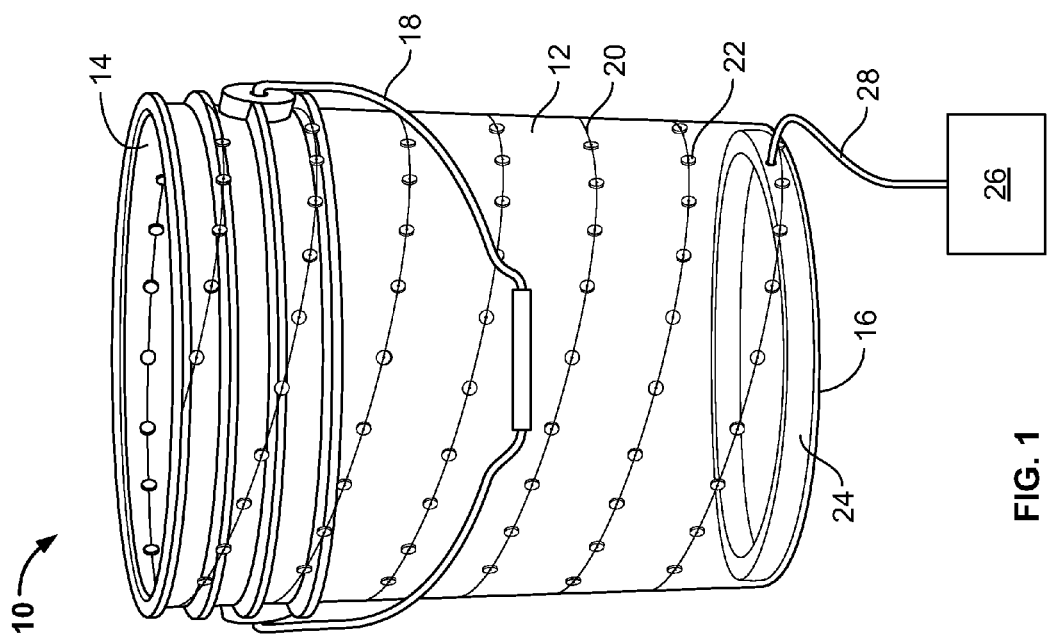
FIG. 1 depicts an embodiment of a container according to the present invention.

As depicted in FIG. 1, an embodiment of a medical device 10 may include a container 12 having a wall 14, a bottom 16, and a carrying handle 18. Embodiments may include a fiber optic cable 20 that wraps up the inner surface of the wall 14. Light terminations 22 may be located on the fiber optic cable 20 inside the container. A heating element 24 may be located around the bottom of the container 12. The fiber optic cable 20 may connect to a light source 26 through a fiber optic connection cable 28.

Bowl.

An embodiment of a medical device may include a bowl and apply an antimicrobial solution that is enhanced with light of a predetermined wavelength. An embodiment may include a bowl, such as a round, open-top container that retains an antimicrobial solution. The bowl may be made of generally watertight material so it can retain liquid solution. A fiber optic cable may wrap all around the inside surface of the bowl, with light terminations spaced along the fiber optic cable. the fiber optic cable has a plurality of light terminations so that an antimicrobial solution in the bowl is lighted with light from the cable so as to substantially surround an item immersed in the bowl. The fiber optic cable may have a plurality of light terminations so that an antimicrobial solution in the bowl is lighted with light from the cable so as to substantially surround an item immersed in the bowl. An embodiment may include a heating element at the bottom of the bowl. The bowl may have a stand or base, and the heating element may be located in the base. The fiber optic cable may connect through a connection cable to a light source. The light source may have an on/off switch and may have a timer control. Embodiments may include a control box that includes the light and heating power source, such as batteries or a connection to wall power. Embodiments of a control box may also include controls for turning the light or heater on or off, setting of timers, and status display. A control box may include receptacles or cables for interfacing with the rest of the medical device, such as a combined interface for both fiber optics and heater power.

To use an embodiment, a user may warm antimicrobial solution in the bowl using the heating element, immerse a body part such as fingers into the antimicrobial solution, and turn on the light source. The user may utilize a control box to turn on or off, or set timers for, the light source, the heater power, or both.

As depicted in FIG. 2, an embodiment of a medical device 30 may include a bowl 32 with a fiber optic cable 34 that wraps around an inside surface 36 of the bowl 32. The fiber optic cable 34 may have light terminations 38. Embodiments may have a base 40, which may contain a heating element 42. The fiber optic cable 34 may connect to a light source 44 through a fiber optic connection cable 46. The light source 44 may include an off/off switch 48 or a timer control 49.

Full Body Suit.

An embodiment of a medical device may include a full body suit with tubing to carry a light-enhanced antimicrobial mist or solution to a user wearing the suit. An embodiment of a suit may include a one-piece garment that generally retains air around the user's body. Embodiments of a full body suit may include a portion that covers at least a user's torso. Embodiments my further include portions to cover a user's legs, feet, arms, head, or hands. Embodiments may have collars, cuffs, or elastic portions that fit against the user to help retain the mist. The portions cooperate to provide a garment that retains the antimicrobial mist within the suit when the suit is worn. A fiber optic cable may wrap around the inside of the suit. A full body suit may include sleeves with gloves or mittens, pants with feet, and a hood with fiber optic cable spaced along the inner fabric of the suit, or otherwise within or on the fabric. Embodiments of gloves, mittens, or feet may help retain the mist within the suit, and may be integrated with the rest of the suit or removable. Embodiments of integrated portions may include fiber optic cable like the rest of the suit. Embodiments of removable portions may lack fiber optic cable, or may include fiber optic cable that can be connected to the fiber optic cable in the sleeves or pants. The fiber optic cable may have light terminations spaced along the fiber optic cable inside the suit. An embodiment may include a heating element inside the body suit, such heating wires embedded in the fabric of the suit. Embodiments may include an input tube or input tubing to carry antimicrobial mist into the suit, an area within the suit to circulate the mist against the user, and an exhaust tube or exhaust tubing to allow air or mist out of the suit. Embodiments of tubing may include an input tube on one side of the torso and an output tube on the opposite side, such as input and output tubes on opposite shoulders.

To use an embodiment, a user may put on the garment, add anti-microbial mist using the input tube, allow the mist to circulate within the suit, and turn on the light source. The user may simultaneously input and output antimicrobial mist to circulate through the suit. The user may power on the heating element to warm the mist.

Figure 3:
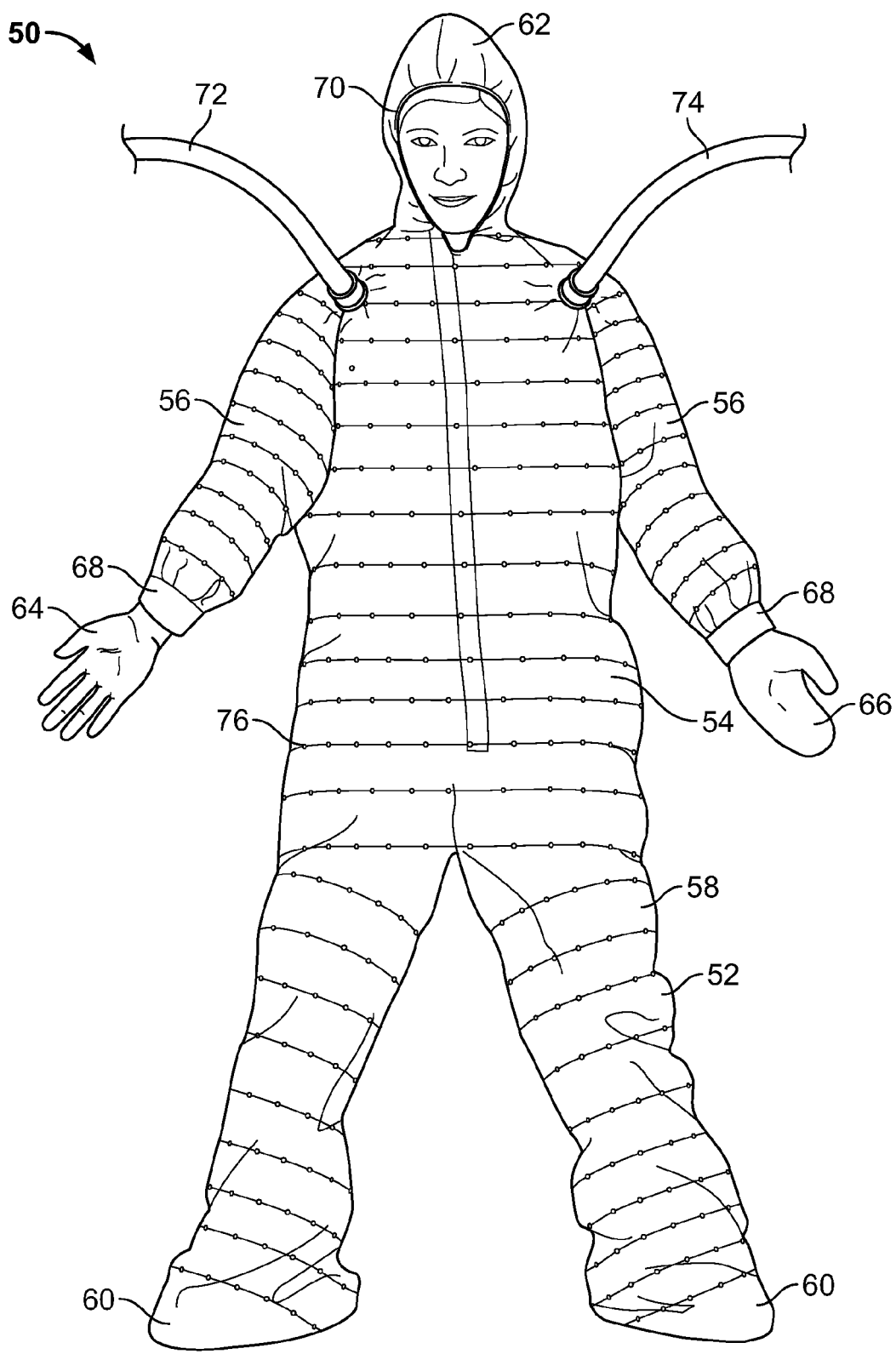
FIG. 3 depicts an embodiment of a full body suit according to the present invention.

As depicted in FIG. 3, an embodiment of a medical device 50 may include a full body suit 52 having an integrated torso portion 54, sleeves 56, pants 58, feet 60, and a hood 62, and removable gloves 64 or mittens 66. The sleeves 56 may have cuffs 68 to tighten against the user's wrists. The hood 62 may have elastic portions 70 to tighten against the user's face. Embodiments may include an input tube 72, such as on one shoulder of the torso portion 54, and an exhaust tube 74 on the opposite shoulder of the torso portion 54. Embodiments may include a fiber optic cable 76 spaced along the inner fabric of the suit 52. Light terminations 78 may be located on the fiber optic cable 76 inside the suit 52. A heating element 80 may be embedded within the fabric of the suit 52. The fiber optic cable 76 or heating element 80 or both may connect to a light source 82 through a fiber optic connection cable 84.

Garments.

An embodiment of a medical device may include a body part covering or garment and apply a light-enhanced antimicrobial mist or solution to a user wearing the covering.

An embodiment of a body part covering may include a section of garment that is shaped and adapted to cover a particular part of a human body. Embodiments of a body part covering may include arm sleeves, a gloves, toe caps, and stockings. Embodiments of body part coverings connected to a light source. Coverings may have light emitting terminations throughout the coverings, and may have heating element. Embodiments may include an arm sleeve that covers the elbow and adjacent portions of a user's arm. Embodiments may include a glove that covers a user's hand and fingers. Embodiments may have open fingers or open finger tips. Embodiments may include a toe cap that covers the front portion of a user's foot, including the toes. Embodiments may include a stocking, such as a thigh-high stocking, a pair of matched stockings, or a one-foot stocking with a waist band. Embodiments of stockings may cover the toes, or may be open at the toe. Embodiments may cover a user's toes, or the toes may be open. Embodiments may include heating elements. Embodiments may include an external light source with a fiber optic connection cable.

Figure 4A:
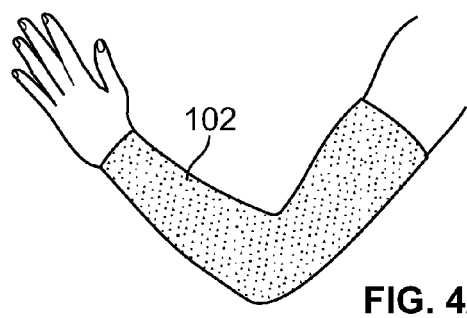
FIG. 4A-4E depict embodiments of garments according to the present invention.
Figure 4B:
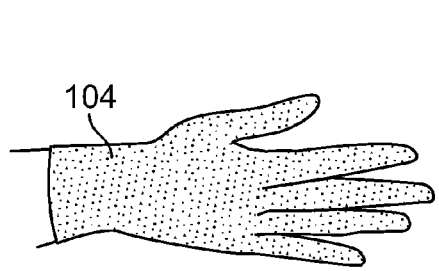
Figure 4C:
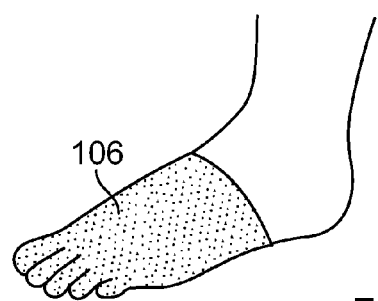
Figure 4D:
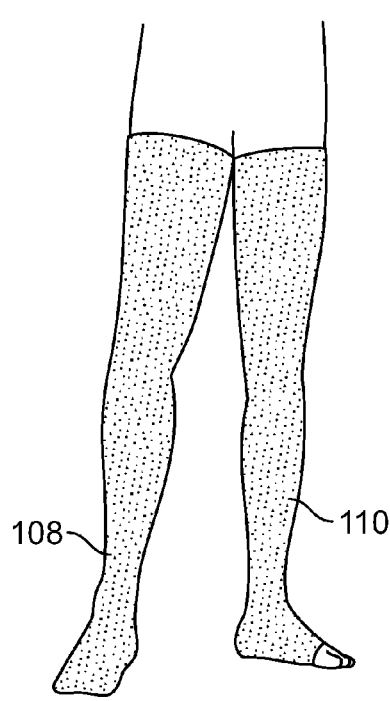
Figure 4E:
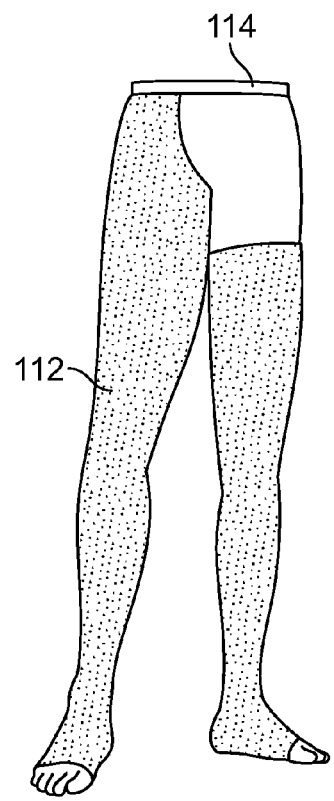

FIGS. 4A, 4B, 4C, 4D and 4E depict embodiments of a medical device including a garment to carry light-enhanced antimicrobial solution to a user wearing the garment. FIG. 4A depicts an embodiment of an arm sleeve 102. FIG. 4B depicts an embodiment of a glove 104. FIG. 4C depicts an embodiment of a toe cap 106. FIG. 4D depicts an embodiment of a thigh-high stocking with a toe covering 108 or without a toe covering 110. FIG. 4E depicts an embodiment of a one foot stocking 112 with waist band 114.

To use an embodiment, a user may put on the garment with anti-microbial solution, and turn on the heater or light source or both.

Helmet.

An embodiment of a medical device may include a helmet to apply an antimicrobial solution to a user's head, while exposing the head to a certain, predetermined wavelength of light. An embodiment may include a helmet, such as a motorcycle or sports helmet that provides protection to at least the upper portion of a user's head. Embodiments may include a lining that retains an antimicrobial solution. A fiber optic cable may wrap around the inside surface of the helmet, with light terminations spaced along the fiber optic cable. Embodiments may include a heating element having wires that become warm. The fiber optic cable may connect through a connection cable to a light source, which may have an on/off switch or a timer control.

To use an embodiment, a user may warm antimicrobial solution in the helmet using the heating element, put the helmet on the user's head, and turn on the light source.

Figure 5:
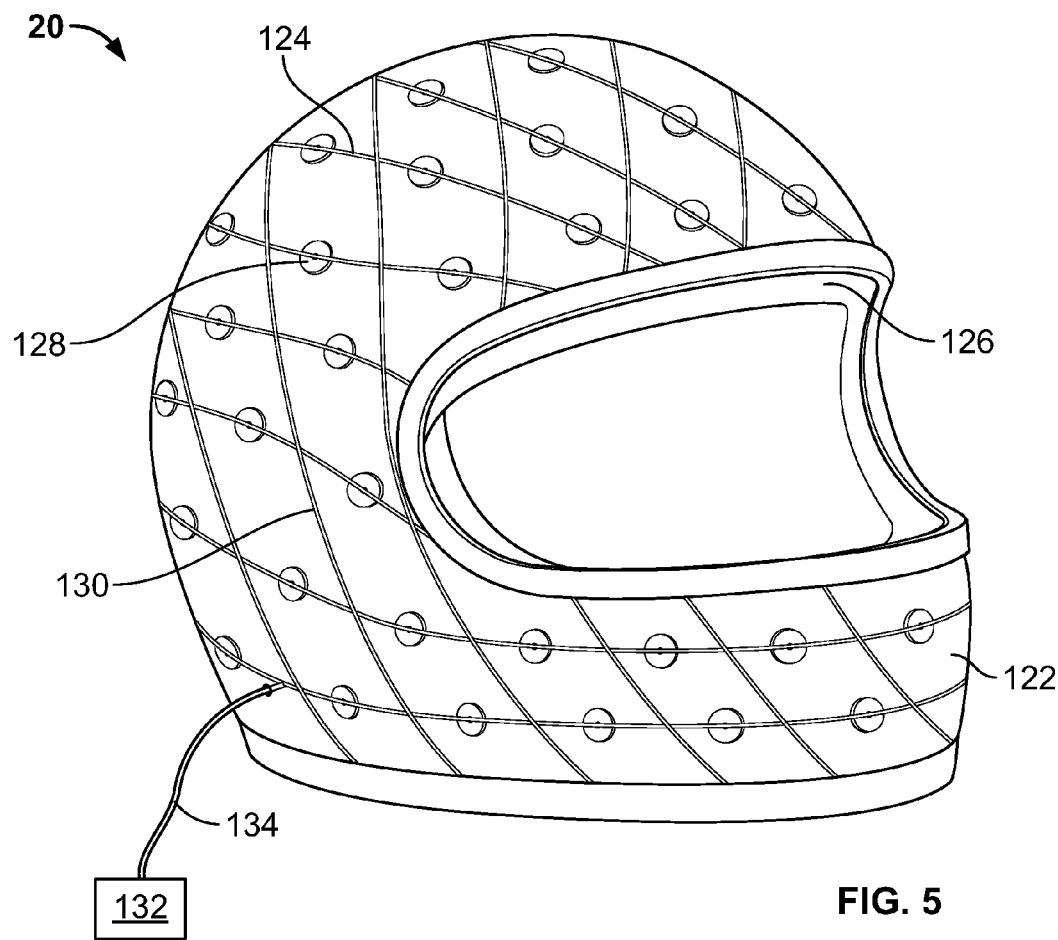
FIG. 5 depicts an embodiment of a helmet according to the present invention.

As depicted in FIG. 5, an embodiment of a medical device 120 may include a helmet 122 with a fiber optic cable 124 that wraps around an inside surface 126 of the helmet 122. The fiber optic cable 124 may have light terminations 128. Embodiments may include heating elements 130 which may include wires in a lining of the helmet. The fiber optic cable 124 may connect to a light source 132 through a fiber optic connection cable 134.

Catheter.

An embodiment of a medical device may include a catheter that can be inserted into a user's body to dispense antimicrobial fluid. Embodiments may also dispense other medicines or fluids, or may be used in a surgical procedure. An embodiment of a catheter may include a light source running into a fiber optic cable, a catheter tube, a mesh to dispense antimicrobial solution, and a termination emitting light. The antimicrobial solution may pass into a first end of the catheter tube, which may be a thin tube or canal down the center of the catheter, made of medical grade materials. Embodiments may receive medicine or antimicrobial solution in one end of the tube, which is dispensed out of a mesh near an opposite or distal end of the tube. Embodiments may include an integrated heating element to warm the antimicrobial solution while in use, or a separate heater to warm the antimicrobial solution before use. Embodiments may include a thin fiber optic cable inside the catheter tube, or the catheter tube itself may be made of fiber optic material so that the tube conducts both light and antimicrobial solution. One or more light terminations may be positioned at the end of the tube, near the mesh portion so that the light shines onto the antimicrobial solution when the solution is dispensed into the user. Embodiments may include a light emitting cable that is integrated with the catheter, or a light emitting cable that is separate from the catheter tube carrying the antimicrobial solution.

To use the device, the catheter may be inserted into a body cavity, and may be used for purposes such as drainage or administration of therapeutic materials before or after the device is used to apply antimicrobial solution. Antimicrobial solution may be preheated with the separate heating element, pumped into the catheter, and dispensed into the user's body. The light may be turned on to supercharge the antimicrobial material while it is dispensed or immediately after it is dispensed and the catheter may be left in place until the treatment is completed.

Figure 6:
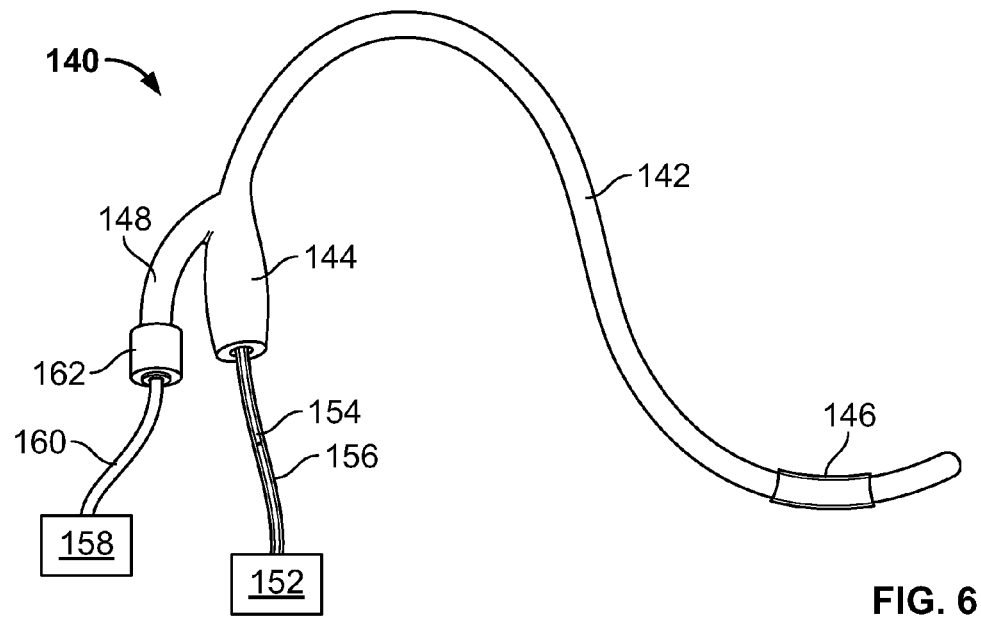
FIG. 6 depicts an embodiment of a catheter according to the present invention.

As depicted in FIG. 6 an embodiment of a medical device 140 may include a catheter 142 having a catheter tube 144, a mesh dispenser screen 146, and a fiber optic cable 148 having one or more light terminations 150. A heating element 152 may be external to the catheter tube 144, and may provide heated antimicrobial solution 154 through an input tube 156. A light source 158 may be connected through a fiber optic connection cable 160 to the fiber optic cable 148 with a fiber optic connection interface 162.

I claim:

1. A device comprising:
a solution retainer adapted to retain an antimicrobial solution against a user;
a fiber optic cable that wraps around an inner surface of the solution retainer;
a light termination on the fiber optic cable that provides light from the fiber optic cable to the antimicrobial solution in the solution retainer; and
a light source that provides a light of a predetermined wavelength to the fiber optic cable.

2. The device of claim 1, further comprising:
a heating element that warms the antimicrobial solution.

3. The device of claim 1, wherein:
the solution retainer includes a container comprising a wall, a bottom, and a carrying handle; and
the fiber optic cable wraps up an inner surface of the wall.

4. The device of claim 3, further comprising:
a heating element located inside the container at the bottom of the container that warms the antimicrobial solution.

5. The device of claim 3, further comprising:
a heating element including a heating wire that wraps up the inner surface of the wall of the container adjacent to the fiber optic cable.

6. The device of claim 1, wherein:
the solution retainer includes a bowl having an open top and a base beneath the bowl;
wherein the fiber optic cable wraps up an inner surface of the bowl; and
the fiber optic cable has a plurality of light terminations so that an antimicrobial solution in the bowl is lighted with light from the cable so as to substantially illuminate an item immersed in the bowl from all sides.

7. The device of claim 6, further comprising:
a heating element in the base the heats the antimicrobial solution.

8. The device of claim 1, wherein:
the solution retainer includes a body suit that covers at least a user's torso; and
the fiber optic cable wraps up an inner surface of the suit.

9. The device of claim 1, wherein the solution retainer includes a full body suit, further comprising:
an input tube to receive an antimicrobial mist;
an area within the suit to circulate the mist against a user; and
an exhaust tube to the mist out of the suit.

10. The device of claim 9, further comprising:
a heating element including a heating wire in a fabric of the suit that warms the antimicrobial solution.

11. The device of claim 1, wherein the solution retainer includes an arm sleeve to cover and apply light-enhanced antimicrobial solution to an arm of a user.

12. The device of claim 1, wherein the solution retainer includes a glove to cover and apply light-enhanced antimicrobial solution to a hand or a portion of user's hand.

13. The device of claim 1, wherein the solution retainer includes a leg stocking to cover and apply light-enhanced antimicrobial solution to a leg or a portion of a user's leg.

14. The device of claim 1, wherein the solution retainer includes a toe cap to cover and apply light-enhanced antimicrobial solution to one or more of a user's toes.

15. The device of claim 1, wherein the solution retainer includes a helmet to cover and apply light-enhanced antimicrobial solution to a user's head.

16. The device of claim 1, wherein:
the solution retainer includes
a catheter tube that receives the antimicrobial solution at a first end; and
a mesh on the catheter tube near a second end opposite the first end, to dispense antimicrobial solution into the user;
wherein the light termination is located on the fiber optic cable near the mesh.

17. The device of claim 16, further comprising:
a heating element that warms the antimicrobial solution as it is dispensed into the user.

* * * * *